(12) United States Patent
Mourelle et al.

(10) Patent No.: US 11,202,814 B2
(45) Date of Patent: Dec. 21, 2021

(54) COMPOSITIONS FOR ATOPIC SKIN

(71) Applicant: INFINITEC ACTIVOS, S.L., Barcelona (ES)

(72) Inventors: Marisabel Mourelle, Barcelona (ES); Aimée Vasconcelos, Barcelona (ES); Ramona Galatola, Barcelona (ES)

(73) Assignee: INFINITEC ACTIVOS, S.L., Barcelona (ES)

( * ) Notice: Subject to any disclaimer, the term of this patent is extended or adjusted under 35 U.S.C. 154(b) by 0 days.

(21) Appl. No.: 16/264,993

(22) Filed: Feb. 1, 2019

(65) Prior Publication Data
US 2019/0240271 A1 Aug. 8, 2019

(30) Foreign Application Priority Data
Feb. 2, 2018 (EP) .................................... 18382058

(51) Int. Cl.
| | | |
|---|---|---|
| *A61K 36/15* | (2006.01) | |
| *A61P 17/00* | (2006.01) | |
| *A61K 47/24* | (2006.01) | |
| *A61K 9/00* | (2006.01) | |
| *A61K 36/9066* | (2006.01) | |
| *A61K 47/44* | (2017.01) | |
| *A61K 31/12* | (2006.01) | |
| *A61K 9/51* | (2006.01) | |
| *A61K 9/127* | (2006.01) | |
| *A61K 31/121* | (2006.01) | |

(52) U.S. Cl.
CPC ............ *A61K 36/15* (2013.01); *A61K 9/0014* (2013.01); *A61K 9/1272* (2013.01); *A61K 9/5123* (2013.01); *A61K 31/12* (2013.01); *A61K 31/121* (2013.01); *A61K 36/9066* (2013.01); *A61K 47/24* (2013.01); *A61K 47/44* (2013.01); *A61P 17/00* (2018.01)

(58) Field of Classification Search
None
See application file for complete search history.

(56) References Cited

U.S. PATENT DOCUMENTS

| | | |
|---|---|---|
| 2011/0129546 A1 | 6/2011 | Millet |
| 2012/0177586 A1 | 7/2012 | Mehta et al. |
| 2013/0052271 A1* | 2/2013 | Sternasty ............... A61K 35/35 424/523 |

FOREIGN PATENT DOCUMENTS

EP 2311454 A2 4/2011

OTHER PUBLICATIONS

Bito, Toshinori, et al.; "Pine Bark Extract Pycnogenol Downregulates IFN-gamma-Induced Adhesion of T Cells to Human Keratinogytes By Inhibiting Inducible ICAM-1 Expression," Free Radical Biology & Medicine, 2000, pp. 219-227, vol. 28.

Vaughn, Alexandra R. et al; "Effects of Turmeric (*Curcuma longa*) on Skin Health: A Systematic Review of the Clinical Evidence," Phytotherapy Research, 2016, pp. 1243-1264, vol. 30.

European Search Report, dated Jul. 19, 2018.

* cited by examiner

*Primary Examiner* — Terry A McKelvey
*Assistant Examiner* — Catheryne Chen
(74) *Attorney, Agent, or Firm* — Tristan A. Fuierer; Olive Law Group, PLLC

(57) ABSTRACT

The present invention provides topical compositions comprising *Pinus pinaster* bark extract and curcumin, particularly in microcapsules and/or nanocapsules comprising phospholipids, and to their pharmaceutical use for the prevention and/or treatment of atopic dermatitis.

16 Claims, No Drawings

COMPOSITIONS FOR ATOPIC SKIN

CROSS REFERENCE TO RELATED APPLICATIONS

This application is filed under 35 U.S.C. § 119(a) and claims priority to European Patent Application No. EP18382058.8, filed Feb. 2, 2018 and entitled "Compositions for Atopic Skin" in the name of Marisabel MOURELLE, which is incorporated herein by reference in its entirety.

FIELD OF THE INVENTION

The present invention relates to the field of pharmacy and cosmetics, in particular, it relates to compositions comprising *Pinus pinaster* bark extract and curcumin, particularly in microcapsules and/or nanocapsules, and to their pharmaceutical use for the prevention and/or treatment of atopic dermatitis.

BACKGROUND OF THE INVENTION

Atopic dermatitis is very common disease that affects the skin. It occurs equally in males and females. Although atopic dermatitis may occur at any age, it most often begins in infancy and childhood. Onset after age 30 is less common and is often caused by exposure of the skin to harsh or wet conditions. As some children with atopic dermatitis grow older, their skin disease improves or disappears altogether, although their skin often remains dry and easily irritated. In others, atopic dermatitis continues to be a significant problem in adulthood. People who live in cities and in dry climates appear more likely to develop this condition. Atopic dermatitis is frequently associated with other allergic disorders, especially asthma and hay fever.

Symptoms of atopic dermatitis include: inflammation of the skin, patches of skin that are red or brownish, itchy skin, especially at night, and dry cracked or scaly skin. Although each person with atopic dermatitis experiences a unique combination of symptoms, which may vary in severity over time, the most common ones are dry, itchy skin and rashes on the face, inside the elbows and behind the knees, and on the hands and feet. Itching is the most important symptom of atopic dermatitis. Scratching and rubbing in response to itching irritates the skin, increases inflammation, and actually increases itchiness. Itching is a particular problem during sleep when conscious control of scratching is lost. The appearance of the skin that is affected by atopic dermatitis depends on the amount of scratching and the presence of secondary skin infections. The skin may be red and scaly or thick and leathery, contain small raised bumps, or leak fluid and become crusty and infected. Other skin features that may appear in some subject suffering from atopic dermatitis are:

- atopic pleat (Dennie-Morgan fold): an extra fold of skin that develops under the eye
- cheilitis: inflammation of the skin on and around the lips
- hyperlinear palms: increased number of skin creases on the palms
- hyperpigmented eyelids: eyelids that have become darker in color from inflammation or hay fever
- ichthyosis: dry, rectangular scales on the skin
- keratosis pilaris: small, rough bumps, generally on the face, upper arms, and thighs
- lichenification: thick, leathery skin resulting from constant scratching and rubbing
- papules: small raised bumps that may open when scratched and become crusty and infected
- urticaria: hives (red, raised bumps) that may occur after exposure to an allergen, at the beginning of flares, or after exercise or a hot bath.

The skin of people with atopic dermatitis is more prone to irritation and infections. The outer layer of skin, called the epidermis, is divided into two parts: an inner part containing moist, living cells, and an outer part, known as the horny layer or stratum corneum, containing dry, flattened, dead cells. Under normal conditions the stratum corneum acts as a barrier, keeping the rest of the skin from drying out and protecting other layers of skin from damage caused by irritants and infections. When this barrier is damaged, irritants act more intensely on the skin and the person's skin is more likely to become infected by bacteria or viruses.

In most cases, there are periods of time when the disease is worse (exacerbations or flares) followed by periods when the skin improves or clears up entirely (remissions).

Atopic dermatitis poses a serious and often chronic impairment of the quality of life of the affected subjects. An infant with atopic dermatitis may be restless and irritable because of the itching and discomfort. Atopic dermatitis also accounts for high costs in medical treatments and emotional suffering of patients. Currently, there is no known cure, although treatments may reduce the severity and frequency of flares. A variety of medications are used to manage atopic dermatitis. Corticosteroid creams and ointments have been used for many years to treat atopic dermatitis. However, due to their side effects, these medications are used only in resistant cases and only given for short periods of time. Certain antihistamines that cause drowsiness can reduce nighttime scratching and allow more restful sleep when taken at bedtime, but they are not as potent as other agents and may be used merely as supplemental therapy. Topical calcineurin inhibitors are also used since they decrease inflammation in the skin and help prevent flares. However, these compounds have undesired side effects. Other treatment options include barrier repair moisturizers to reduce water loss and work to rebuild the skin as well as phototherapy, but these options can only be effective for mild to moderate dermatitis. Due to the drawbacks of the known treatments for managing atopic dermatitis, researchers are trying to find new therapies. Among other alternatives, it has been suggested to use a pine bark extract in the treatment of inflammatory skin diseases such as atopic dermatitis due to its anti-inflammatory properties in keratinocytes [Bito, T. et al., Free Radical Biology Medicine, 2000, 28(2), 219-227]. It has also been reported that curcumin may provide a therapeutic benefit in atopic dermatitis [Vaughn, A. R. et al., Phytotherapy Research, 2016, 30(8), 1243-1264]. However, further research is needed for new therapies.

In view of the above, it can be seen that there still remains a need for treatments for atopic dermatitis, in particular for a treatment that is safe, effective, easy to use and has a reduced cost.

SUMMARY OF THE INVENTION

The inventors have surprisingly found that compositions comprising *Pinus pinaster* pine bark extract and curcumin show a synergistic effect in inhibiting inflammation in human dermal fibroblasts. Due to this synergy, the amount of actives needed for achieving the desired pharmaceutical effect is decreased, thus reducing the cost and attenuating any potential side effects. Compositions comprising *Pinus pinaster* bark extract and curcumin do also favour the formation of a film of lipids on the surface of the skin which reduced the water loss, thus improving skin hydration. This effect is particularly enhanced when the *Pinus pinaster* bark extract and curcumin are encapsulated in microcapsules or nanocapsules comprising phospholipids, preferably from marine origin. These loaded capsules do also act as a barrier that prevents the entry of bacteria and allergens and strengthens the immune system. Thus, the compositions of the invention are suitable for providing a safer management of atopic dermatitis avoiding the use of prior art treatments that provide undesirable side effects, while being effective, easy to use and/or have a reduced cost.

Thus, in a first aspect, the present invention relates to a composition comprising *Pinus pinaster* bark extract and curcumin wherein the ratio by weight of curcumin to *Pinus pinaster* bark extract is from 1:10 to 1:1000.

In a second aspect, the present invention relates to a microcapsule and/or nanocapsule comprising a composition as defined in the first aspect.

In a third aspect, the present invention relates to a composition comprising microcapsules and/or nanocapsules as defined in the second aspect.

In a fourth aspect, the present invention relates to a method of treating patients with atopic dermatitis by topically applying to said patient a composition as defined in the first or third aspect, or microcapsule and/or nanocapsule as defined in the second aspect.

In a fifth aspect, the present invention relates to a method of reducing redness and skin water-loss in a patient prone to atopic dermatitis by topically applying a composition a composition as defined in the first or third aspect, or microcapsule and/or nanocapsule as defined in the second aspect.

DETAILED DESCRIPTION OF THE INVENTION

The first aspect of the present invention relates to a composition comprising *Pinus pinaster* bark extract and curcumin wherein the ratio by weight of curcumin to *Pinus pinaster* bark extract is from 1:10 to 1:1000.

The term "*Pinus pinaster* bark extract" is a standardized plant extract (*Pinus pinaster* bark extract, 95% Procyanidin) obtained from the bark of *Pinus pinaster* (formerly known as *Pinus maritima*). The fresh bark is powdered and extracted with ethanol and water. After purification of the raw extract, the aqueous solution of the extracted constituents is spray-dried. The resulting fine brownish powder is stable if stored in a dry, dark environment. The extract comprises phenolic acids, catechin, taxifolin and procyanidins, as described in P. J. Rohdewald [*Encyclopedia of Dietary Supplements*, 2005, Marcel Dekker, 545-553]. The phenolic acids are derivatives of benzoic acid (p-hydroxybenozic acid, protocatechic acid, vanillic acid and gallic acid) or of cinnamic acid, p-cumaric acid, caffeic acid, and ferulic acid. Glycosides and glycose esters of these phenolic acids are also found. Catechin is found as the main monomeric procyanindin, while epicatechin is present in traces. Taxifolin is available in free form and as taxifolin glucoside. This extract is characterized by having from 80% to 100% of procyanidins, preferably from 90% to 100%, more preferably from 92% to 98%, still more preferably from 94% to 96%, wherein the procyanidins comprise catechin and epicatechin subunits with varying chain lengths, from dimers up to 12 monomeric units.

The term "curcumin" refers to diferuloylomethane, i.e. (E,E)-1,7-bis(4-hydroxy-3-methoxyphenyl)-1,6-heptadiene-3,5-dione, which is a phytopolyphenol pigment isolated from turmeric (*Curcuma longa*).

In a preferred embodiment, the ratio by weight of curcumin to *Pinus pinaster* bark extract is from 1:20 to 1:1000, preferably from 1:50 to 1:200, more preferably from 1:70 to 1:125.

In a particular embodiment, the composition further comprises water and/or dimethylsulfoxide. In a preferred embodiment, the composition comprises water. In another particular embodiment, the composition comprises dimethylsulfoxide. In a further particular embodiment, the composition comprises water and dimethylsulfoxide.

In a particular embodiment, the composition of the invention comprises:
from 0.1 to 10 wt % of *Pinus pinaster* bark extract,
from 0.001 to 0.1 wt % of curcumin, and
water.

In another particular embodiment, the composition of the invention comprises:
from 0.5 to 2 wt % of *Pinus pinaster* bark extract,
from 0.005 to 0.015 wt % of curcumin, and
water.

In the above compositions of the invention, water is preferably present in an amount of at least 70 wt %, preferably at least 75 wt %, more preferably at least 80 wt %, even more preferably at least 85 wt %.

In a particular embodiment, the composition of the invention is devoid of indomethacin, sage extract and/or ginger extract.

The above compositions may be prepared by mixing the ingredients, preferably with stirring at room temperature (20-25° C.).

The compositions described above have a synergistic effect in inhibiting inflammation in human dermal fibroblasts. These compositions do also favour the formation of a film of lipids on the surface of the skin which reduced the water loss, thus improving skin hydration. The inventors have also surprisingly found that this effect is particularly enhanced when the above described compositions are encapsulated in microcapsules or nanocapsules comprising phospholipids, preferably from marine origin.

Therefore, the second aspect relates to a microcapsule and/or nanocapsule comprising a composition as defined in the first aspect.

The terms "microcapsule" and "nanocapsule", also called herein "capsules", refer to capsules with a size distribution from 10 to 10000 nm. In one embodiment the capsules have a size distribution from 50 to 5000 nm, from 100 to 1000 nm, preferably from 150 to 450 nm and more preferably from 200 to 400 nm. The size of the capsules can be determined by dynamic light scattering (DLS) using a Zetasizer nano ZS (Malvern Instruments, Malvern, UK) at 25° C. The measurements are performed on samples previously diluted in water (Millipore Corporation, Billerica, Mass., USA).

In a preferred embodiment, the microcapsules and/or nanocapsules of the invention comprise a lipid bilayer of a phospholipid. This lipid bilayer forms the shell of the microcapsules and/or nanocapsules of the invention.

The term "phospholipid" refers to a lipid that contains a glycerol attached by means of ester bonds to two fatty acid groups and to one phosphate group, said phosphate group being optionally further attached through a phosphoester bond to another group such as choline, ethanolamine, inositol or serine, or to lipids that have a phosphocholine or phosphoethanolamine moiety attached through an ester bond to the 1-hydroxy group of a ceramide (a ceramide being a sphingosine bonded to a fatty acid). Examples of phospholipids are phosphatidylcholine (PC), phosphatidylethanolamine (PE), phosphatidylinositol (PI), phosphatidylserine (PS), and phosphatidic acids, whose structures are depicted below and wherein each R represents independently a fatty acid.

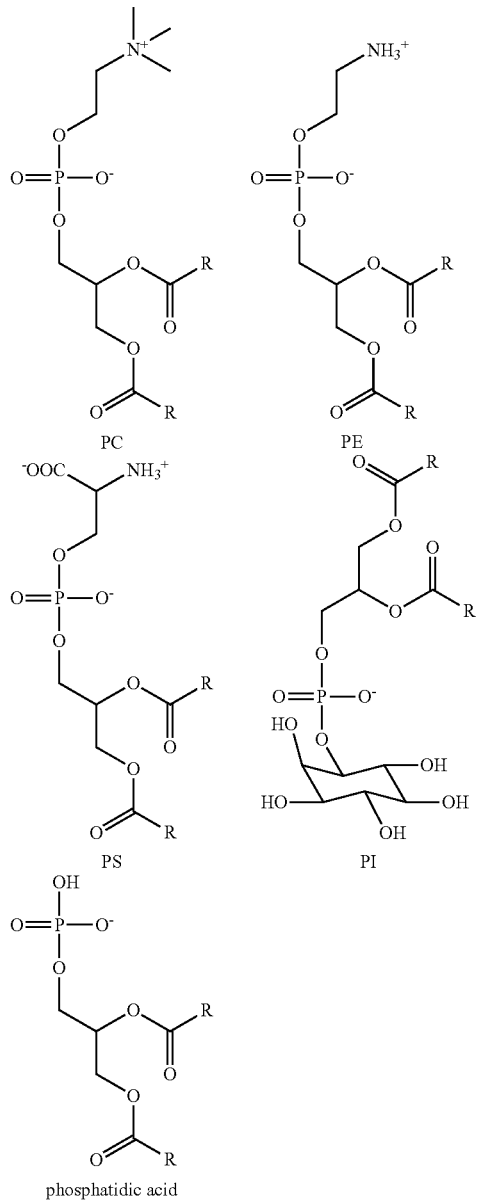

In one embodiment, the phospholipid is selected from the group consisting of phosphatidylcholine, phosphatidylethanolamine, phosphatidylinositol, phosphatidylserine, phosphatidic acid and mixtures thereof, preferably the phospholipid comprises phosphatidylcholine, more preferably, the phospholipid comprises phosphatidylcholine and phosphatidylethanolamine, still more preferably the phospholipid comprises phosphatidylcholine, phosphatidylethanolamine, phosphatidylinositol and phosphatidic acid. In a particular embodiment, the phospholipid comprises at least 5 wt % of phosphatidylcholine; preferably at least 6.5 wt % of phosphatidylcholine; more preferably from 5 to 10 wt % of phosphatidylcholine; more preferably from 6.5 to 10 wt % of phosphatidylcholine; still more preferably from 5 to 10 wt % of phosphatidylcholine, from 0.5 to 1 wt % of phosphatidylethanolamine, optionally from 0.05 to 0.5 wt % of phosphatidylinositol (i.e. PI may be absent or present and when present it is in the indicated amounts) and optionally from 0.05 to 0.5 wt % of phosphatidic acid (i.e. phosphatidic acid may be absent or present and when present it is in the indicated amounts); even more preferably from 6.5 to 10 wt % of phosphatidylcholine from 0.5 to 1 wt % of phosphatidylethanolamine, from 0.05 to 0.5 wt % of phosphatidylinositol and from 0.05 to 0.5 wt % of phosphatidic acid. The amounts by weight (wt %) are expressed with respect to the total weight of the phospholipid.

In a particular embodiment, the ratio by weight of *Pinus pinaster* bark extract to phospholipid is from 1:1 to 10:1, preferably from 1:1 to 6:1, more preferably from 2:1 to 4:1, even more preferably from 2.5:1 to 3.5:1.

In a particular embodiment, the ratio by weight of phospholipid to curcumin is from 1:1 to 100:1, preferably from 1:1 to 50:1, more preferably from 20:1 to 40:1, even more preferably from 30:1 to 35:1.

The term "fatty acid" refers to a saturated or unsaturated straight chain hydrocarbon having 6 or more carbon atoms in the chain, such as from 6 to 26 carbon atoms, possessing a carboxyl group at one end. Examples of saturated fatty acids are caprylic acid, capric acid, lauric acid, myristic acid, palmitic acid, stearic acid, arachidic acid, behenic acid, lignoceric acid, cerotic acid and the like. Unsaturated fatty acids have one or more double bonds (C=C), preferably one, two, three, four, five or six double bonds. Examples of unsaturated fatty acids are myristoleic acid, palmitoleic acid, sapienic acid, oleic acid, elaidic acid, vaccenic acid, linoleic acid, linoelaidic acid, γ-linolenic acid, arachidonic acid, eicosapentaenoic acid, erucic acid, docosahexaenoic acid, hexadecatrienoic acid, stearidonic acid, eicosatrienoic acid, eicosatetranoic acid, heneicosapentaenoic acid, docosapentaenic acid, tetracosapentaenoic acid, tetracosahexaenoic, γ-linolenic acid, calendic acid, eicosadienoic acid, dihomo-γ-linolenic acid, docosadienoic acid, adrenic acid, docosapentaenoic acid, tetracosatetraenoic acid, gondoic acid, mead acid, nervonic acid and the like. Unsaturated fatty acids wherein the first double bond exists at the third carbon-carbon bond from the terminal $CH_3$ end of the carbon chain are known as omega-3 fatty acid), wherein the first double bond exists at the sixth carbon-carbon bond from the terminal $CH_3$ end of the carbon chain they are known as omega-6 fatty acid and wherein the first double bond exists at the ninth carbon-carbon bond from the terminal $CH_3$ end of the carbon chain they are known as omega-9 fatty acid. Examples of omega-3 fatty acids, such as α-linolenic acid (ALA), eicosapentaenoic acid (EPA), and docosahexaenoic acid (DHA), hexadecatrienoic acid (HTA), stearidonic acid (SDA), eicosatrienoic acid (ETE), eicosatetranoic acid (ETA), heneicosapentaenoic acid (HPA), docosapentaenic acid (DPA), tetracosapentaenoic acid and tetracosahexaenoic acid and mixtures thereof omega-6 fatty acids, such as linoleic acid (LA), γ-linolenic acid (GLA), calendic acid, eicosadienoic acid, dihomo-γ-linolenic acid (DGLA), arachidonic acid (AA), docosadienoic acid, adrenic acid, docosapentaenoic acid, tetracosatetraenoic acid, tetracosapentaenoic acid, and mixtures thereof omega-9 fatty acids, such as oleic acid, elaidic acid, gondoic acid, mead acid, erucic acid and nervonic acid, and mixtures thereof. Preferably, the fatty acids are selected from the group consisting of palmitic acid, oleic acid, DHA, EPA and mixtures thereof.

The hydrophilic part of the phospholipid bilayer (phospholipid head) is formed by the negatively charged phosphate group and glycerol. The hydrophobic part of the phospholipid bilayer (phospholipid tail) is formed by the fatty acid chains. Water soluble compounds (such as *Pinus pinaster* bark extract) are located in the interior of the capsules, whereas water insoluble compounds (such as curcumin) are located in the region of the hydrophobic tails of the phospholipid bilayer. In addition the microcapsules and/or nanocapsules may comprise vitamin E or an ester thereof and/or astaxanthin. Said vitamin E or an ester thereof and astaxanthin are located in the region of the hydrophobic tails of the phospholipid bilayer.

The term "vitamin E" refers to tocopherols, tocotrienols, including their stereoisomers and mixtures thereof, such as α-tocopherol, β-tocopherol, γ-tocopherol, δ-tocopherol, α-tocotrienol, β-tocotrienol, γ-tocotrienol, δ-tocotrienol, stereoisomers thereof and mixtures thereof; preferably α-tocopherol or a stereoisomer thereof

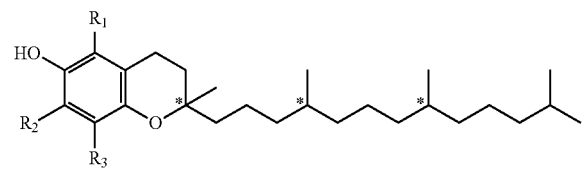

Tocopherols

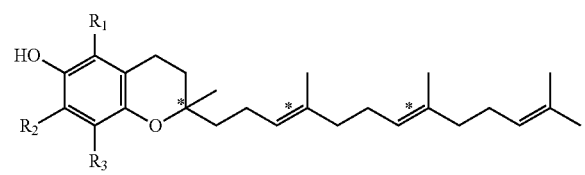

Tocotrienols

"α-Tocopherol" is also known as 2,5,7,8-tetramethyl-2-(4,8,12-trimethyltridecyl)-3,4-dihydrochromen-6-ol and has the structure shown above wherein $R_1$, $R_2$ and $R_3$ are methyl groups. "β-Tocopherol" is also known as 2,5,8-trimethyl-2-(4,8,12-trimethyltridecyl)-3,4-dihydrochromen-6-ol and has the structure shown above wherein $R_1$ and $R_3$ are methyl groups and $R_2$ is a hydrogen atom. "γ-Tocopherol" is also known as 2,7,8-trimethyl-2-(4,8,12-trimethyltridecyl)-3,4-dihydrochromen-6-ol and has the structure shown above wherein $R_2$ and $R_3$ are methyl groups and $R_1$ is a hydrogen atom. "δ-Tocopherol" is also known as 2,8-dimethyl-2-(4,8,12-trimethyltridecyl)-3,4-dihydrochromen-6-ol and has the structure shown above wherein $R_3$ is a methyl group and $R_1$ and $R_2$ is are hydrogen atoms. The tocopherols depicted above have three chiral carbon atoms marked with * in the structure depicted above that may be in R or S configuration, one at position 2 of the 3,4-dihydrochromene ring, one at position 4 of the tridecyl chain and one at position 8 of the tridecyl chain. Examples of stereoisomers of any of the particular tocopherols mentioned above are the 2R,4R,8R-stereoisomers (or RRR), 2R,4S,8R-stereoisomers (or RSR), 2R,4R,8S-stereoisomers (or RRS), 2R,4S,8S-stereoisomers (or RSS), 2S,4R,8R-stereoisomers (or SRR), 2S,4S,8R-stereoisomers (or SSR), 2S,4R,8S-stereoisomers (or SRS) and 2S,4S,8S-stereoisomers (or SSS). When reference is made to tocopherol, α-tocopherol, β-tocopherol, γ-tocopherol and/or δ-tocopherol, the particular stereoisomers and mixtures of stereoisomers are also encompassed.

"α-Tocotrienol" is also known as 2,5,7,8-tetramethyl-2-(4,8,12-trimethyltrideca-3,7,11-trienyl)-3,4-dihydrochromen-6-ol and has the structure above below wherein $R_1$, $R_2$ and $R_3$ are methyl groups. "13-Tocotrienol" is also known as 2,5,8-trimethyl-2-(4,8,12-trimethyltrideca-3,7,11-trienyl)-3,4-dihydrochromen-6-ol and has the structure shown above wherein $R_1$ and $R_3$ are methyl groups and $R_2$ is a hydrogen atom. "γ-Tocotrienol" is also known as 2,7,8-trimethyl-2-(4,8,12-trimethyltrideca-3,7,11-trienyl)-3,4-dihydrochromen-6-ol and has the structure shown above wherein $R_2$ and $R_3$ are methyl groups and $R_1$ is a hydrogen atom. "δ-Tocotrienol" is also known as 2,8-dimethyl-2-(4,8,12-trimethyltrideca-3,7,11-trienyl)-3,4-dihydrochromen-6-ol and has the structure shown above wherein $R_3$ is a methyl group and $R_1$ and $R_2$ is are hydrogen atoms. The tocotrienols depicted above have one chiral carbon atoms marked with * in the structure depicted above that may be in R or S configuration, at position 2 of the 3,4-dihydrochromene ring, and two double bonds marked with * in the structure depicted above that may be in E or Z configuration, one double bond at position 3 of the tridecyl chain and double bond at position 7 of the tridecyl chain. Examples of stereoisomers of any of the above depicted tocotrienols are the 2R,3E,7E-stereoisomers, 2R,3Z,7E-stereoisomers, 2R,3E,7Z-stereoisomers, 2R,3Z,7Z-stereoisomers, 2S,3E,7E-stereoisomers, 2S,3Z,7E-stereoisomers, 2S,3E,7Z-stereoisomers and 2S,3Z,7Z-stereoisomers. When reference is made to tocotrienol, α-tocotrienol, β-tocotrienol, γ-tocotrienol and/or δ-tocotrienol, the particular stereoisomers and mixtures of stereoisomers are also encompassed.

The vitamin E may be present as a single compound and single stereoisomer or as a mixture of different tocopherols and/or tocotrienols and/or stereoisomers thereof.

Esters of vitamin E refer to derivatives of any of the above compounds (tocopherols, tocotrienols, stereoisomers thereof and mixtures thereof), wherein the hydroxyl group (—OH) of the phenol moiety has been replaced with an ester moiety (—OC(=O)R), i.e. tocopheryl and tocotrienyl esters, including stereoisomers thereof and mixtures thereof. Examples of esters of Vitamin E are the acetate (R is —CH₃) and succinate esters (R is —CH₂CH₂COOH), and mixtures thereof, preferably the acetate ester.

The term "astaxanthin" refers to (3S,3'S)-3,3'-dihydroxy-β,β-carotene-4,4'-dione, i.e. (6S)-6-hydroxy-3-[(1E,3E,5E,7E,9E,11E,13E,15E,17E)-18-[(4S)-4-hydroxy-2,6,6-trimethyl-3-oxo-1-cyclohexenyl]-3,7,12,16-tetramethyloctadeca-1,3,5,7,9,11,13,15,17-nonaenyl]-2,4,4-trimethyl-1-cyclohex-2-enone, whose structure is depicted below.

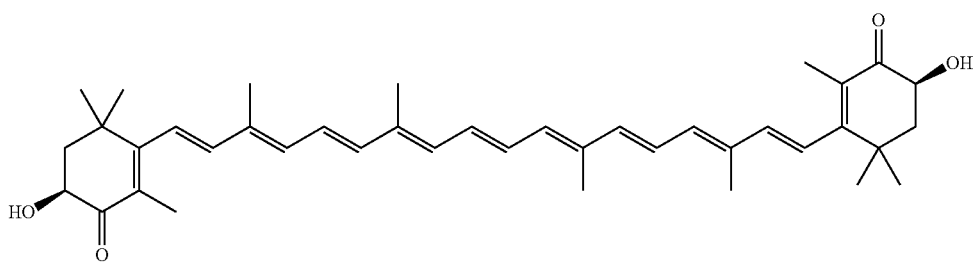 [SMILES: CC1=C(/C=C/C(C)=C/C=C/C(C)=C/C=C/C=C(C)/C=C/C=C(C)/C=C/C2=C(C)C(=O)[C@@H](O)CC2(C)C)C(C)(C)C[C@H](O)C1=O]

The phospholipids of the nanocapsules or microcapsules of the present invention may be obtained from algae such as *Chorella* sp. and *Nannochloropsis salina*. Thus, they comprise fatty acids, in particular omega-3 fatty acids. The phospholipids may be obtained by extraction from algae in 99% ethanol for one hour at 75° C. followed by filtration and removal of the solvent.

In a preferred embodiment, the phospholipids comprise omega-3 fatty acids, preferably selected from the group consisting of eicosapentaenoic acid, docosahexaenoic acid and mixtures thereof.

In a particular embodiment, the phospholipid comprises phosphatidylcholine wherein the fatty acid rests comprise from 1 to 5 wt % EPA and from 5 to 15 wt % DHA with respect to the weight of the phosphatidylcholine.

In a particular embodiment, the microcapsules and/or nanocapsules of the invention comprise:
from 0.1 to 10 wt % of *Pinus pinaster* bark extract,
from 0.001 to 0.1 wt % of curcumin, and
from 0.01 to 10 wt % of phospholipids.

In another particular embodiment, the microcapsules and/or nanocapsules of the invention comprise:
from 0.5 to 2 wt % of *Pinus pinaster* bark extract,
from 0.005 to 0.015 wt % of curcumin, and
from 0.1 to 1 wt % of phospholipids.

The above microcapsules and/or nanocapsules of the invention may further comprise vitamin E or an ester thereof and/or astaxanthin.

In a particular embodiment, the above microcapsules and/or nanocapsules of the invention further comprise maltodextrin. Preferably at least 1 wt % maltodextrin, with respect to the total weight of the composition, preferably from 1 to 5 wt %, more preferably from 3 to 4 wt %.

The microcapsules and/or nanocapsules of the invention may be prepared by dissolving or suspending curcumin and *Pinus pinaster* bark extract in a suitable solvent, such as water and/or MCT, in particular curcumin may be dissolved in MCT, preferably caprylic/capric triglyceride, and the *Pinus pinaster* bark extract may be dissolved in water, followed by mixing and addition of the phospholipids. The resulting mixture is homogenized, preferably using a disperser. The dispersion is preferably carried out at room temperature (20-25° C.).

The capsules of the invention are preferably dispersed in water.

The term "medium chain triglyceride" or "MCT" refers to triglycerides triesters of glycerol and 6-12 carbon fatty acid. The fatty acids found in medium chain triglycerides are called medium chain fatty acids. Like all triglycerides (fats and oils), medium chain triglycerides are composed of a glycerol backbone and three fatty acids. In the case of medium chain triglycerides, 2 or 3 of the fatty acid chains attached to glycerol are medium chain in length. The three fatty acids of the MCT can be the same or different, preferably there are two different fatty acids. Examples of medium fatty acids are caproic or hexanoic acid (C6:0), caprylic or octanoic acid (C8:0), capric or decanoic acid (C10:0) and lauric or dodecanoic acid (C12:0). Preferably, the MCT is caprylic/capric triglyceride. The MCT is located in the phospholipid bilayer. The ratio by weight of curcumin to medium chain triglyceride is from 1:10 to 1:1000, preferably from 1:20 to 1:1000, more preferably from 1:50 to 1:200, more preferably from 1:70 to 1:125.

The microcapsules and/or nanocapsules described above may be formulated in a composition, preferably a composition for topical use. Thus, the third aspect of the present invention relates to a composition comprising the microcapsules and/or nanocapsules described above.

In a particular embodiment, the composition described above contains the microcapsules and/or nanocapsules of the invention dispersed in matrix comprising a pharmaceutically acceptable excipient.

The term "matrix" refers to a continuous phase wherein the capsules of the invention are dispersed.

The term "pharmaceutically acceptable excipient" refers to an inactive substance that can be liquid, solid or semisolid, used as a medium or carrier for the active ingredients of a composition, in particular for the capsules of the invention. Such pharmaceutically acceptable excipients can be liquids, such as water, oils or surfactants, including those of petroleum, animal, plant or synthetic origin, such as for example and in a non-limiting sense peanut oil, soybean oil, mineral oil, sesame oil, castor oils, liquid paraffin, isopropyl myristate, medium chain triglycerides, stearyl alcohol, cetearyl octanoate, polysorbates, sorbitan esters, ether sulfates, ethoxylated fatty alcohols, sulfates, betaines, glucosides, maltosides, fatty alcohols, nonoxinols, poloxamers, polyoxyethylenes, glyceryl stearate, polyethylene glycols, dextrose, glycerol and the like. "Remington's Pharmaceutical Sciences" by E. W. Martin describes examples of suitable excipients.

In a preferred embodiment, the pharmaceutically acceptable excipient is selected from the group consisting of water, humectants, preservatives and mixtures thereof, preferably water.

The term "humectant" refers to a compound that holds and retains moisture. Examples of humectants are glycerin, propanediol, and sorbitol.

The term "preservative" refers to a compound that inhibits or reduces the development of microorganism in the formulation (when compared to the development of microorganism in the absence of said compound). Examples of preservatives are phenoxyethanol; a mixture comprising caprylyl glycol, glyceryl caprylate, glycerin and phenylpropanol; a mixture comprising benzyl alcohol, glyceryl caprylate and glyceryl undecylenate; a mixture comprising 2,2-hexanediol and caprylyl glycol; a mixture comprising phenethyl alcohol and ethylhexylglycerin; a mixture comprising penthylene glycol, caprylyl glycol and ethylhexylglycerin.

In a particular embodiment, the compositions containing the microcapsules and/or nanocapsules of the invention comprise:
from 0.1 to 10 wt % of *Pinus pinaster* bark extract,
from 0.001 to 0.1 wt % of curcumin,
from 0.1 to 10 wt % of MCT (preferably caprylic/capric triglyceride),
from 0.01 to 10 wt % of phospholipids, and
water.

In another particular embodiment, the compositions containing the microcapsules and/or nanocapsules of the invention comprise:
from 0.5 to 2 wt % of *Pinus pinaster* bark extract,
from 0.005 to 0.015 wt % of curcumin,
from 0.5 to 2 wt % of MCT (preferably caprylic/capric triglyceride),
from 0.1 to 1 wt % of phospholipids, and
water.

In a particular embodiment, the above compositions of the invention further comprise maltodextrin. Preferably at least 1 wt % maltodextrin, with respect to the total weight of the composition, preferably from 1 to 5 wt %, more preferably from 3 to 4 wt %.

In the above compositions of the invention, water is preferably present in an amount of at least 70 wt %, preferably at least 75 wt %, more preferably at least 80 wt %, even more preferably at least 85 wt %.

The above described composition may be prepared mixing the microcapsules and/or nanocapsules of the invention with the pharmaceutically acceptable excipients, preferably at room temperature (20-25° C.).

In a preferred embodiment, the compositions of the present invention are suitable for topical use.

The term "topical" is used herein to characterize a composition as being suitable for application in the exterior of the body such as, without limitation, the skin, scalp and nails; and also the application to mucosae such as, without limitation, buccal, nasal or rectal mucosae or to characterize a composition as being suitable for such an application.

The compositions, microcapsules and nanocapsules of the invention are suitable for use in the treatment and/or prevention of atopic dermatitis.

Thus, in a further aspect, the invention relates to a compositions, microcapsules and/or nanocapsules of the invention for use in medicine.

In another aspect, the invention relates to a composition, microcapsule or nanocapsule of the invention for use in use in the treatment and/or prevention of atopic dermatitis, in particular pruritus, atopic eczema, hypersensitivity skin and itching resulting from atopic dermatitis.

In another aspect, the invention relates to the use of a composition, microcapsule or nanocapsule of the invention in the manufacture of a medicament for the treatment and/or prevention of atopic dermatitis, in particular pruritus, atopic eczema, hypersensitivity skin and itching resulting from atopic dermatitis.

In another aspect, the invention relates to a method of treatment and/or prevention of atopic dermatitis, in particular pruritus, atopic eczema, hypersensitivity skin and itching resulting from atopic dermatitis, in a subject in need thereof comprising the administration to said subject of a compositions, microcapsules and/or nanocapsules of the invention.

The term "prevention" refers to the administration of the compositions, microcapsules and/or nanocapsules of the invention in an initial or early stage of atopic dermatitis, or to also avoid its onset.

The term "treatment" is used to designate the administration of the compositions, microcapsules and/or nanocapsules of the invention to control atopic dermatitis progression before or after the clinical signs had appeared. By control of progression it is meant to designate beneficial or desired clinical results including, but not limited to, reduction of symptoms, reduction of the length of the disorder, stabilization pathological state (specifically avoidance of further deterioration), delay in the disorder's progression, improvement of the pathological state and remission (both partial and total).

The term "subject" refers to any human or animal that is suffering from or at risk of suffering from atopic dermatitis. Preferably, the subject is a mammal. The term "mammal" refers to any mammalian species, including but not being limited to domestic and farm animals (cows, horses, pigs, sheep, goats, dogs, cats or rodents), primates, and humans. Preferably, the mammal is a human being.

The compositions of the invention can be administered by different routes such as, without limitation topical route, in particular cutaneous, buccal, nasal or rectal route. In a preferred embodiment they are applied on the skin, i.e. cutaneous route. The compositions of the inventions may be administered one or more times a day, such as 1 or 2, or 1, 2, or 3, or 1, 2, 3 or 4 times a day, preferably 1 or 2 times a day.

The following examples are merely illustrative of certain embodiments of the invention and cannot be considered as restricting it in any way.

EXAMPLES

Example 1. Composition Comprising *Pinus pinaster* Bark Extract and Curcumin

*Pinus pinaster* bark extract solution was prepared by dissolving said extract (obtained from Henkel Corporation) in distilled water and vortexing. Curcumin was prepared by dissolving a said compound (obtained from Sigma-Aldrich) in an aqueous solution of dimethysulphoxide (0.1 wt %) and vortexing. The *Pinus pinaster* bark extract and the curcumin solutions where combined in a ratio of 1:1 by volume so that the final concentration of *Pinus pinaster* bark extract in the composition was 1 wt % and the final concentration of curcumin in the composition was 0.01 wt %, with respect to the total weight of the composition.

Example 2. Capsules Loaded with *Pinus pinaster* Bark Extract and Curcumin

The capsules were prepared by the high shear homogenization method. Briefly, *Pinus pinaster* bark extract (from Henkel Corporation) was dissolved in water. Curcumin (from Sigma-Aldrich) was dissolved in caprylic/capric triglyceride (obtained from Gattefosse). The solutions were mixed vigorously and subsequently the phospholipids from Phosphotech (containing phosphatidylcholine 6.5 wt %, phosphatydylethanolamine 0.5 wt % phosphatydylinositol 0.5 wt %, phosphatidic acid 0.5 wt %, wherein the fatty acid groups of the phospholipids contain palmitic acid 3 wt %, oleic acid 2.5 wt %, EPA 2.5 wt %, DHA 9 wt %, and maltodextrin csp 100 wt %) was added. The resulting capsules suspension was homogenized using ULTRA-TUR- RAX (IKA® T25) at 24,000 rpm. The amount of each ingredient in the resulting composition (capsules dispersed in water) is provided in Table 1 below, wherein the amounts are expressed as wt % with respect to the total weight of the composition.

TABLE 1

|  | Example 2 |
|---|---|
| *Pinus pinaster* bark extract | 1 |
| Curcumin | 0.01 |
| Phosphotech phospholipids | 4 |
| Caprylic/capric triglyceride | 1 |
| Water q.s. | 100 |

The mean particle size was determined via dynamic light scattering using a Zetasizer nano ZS (Malvern Instruments, Malvern, UK) at 25° C. The measurements were performed on samples previously diluted in water (Millipore Corporation, Billerica, Mass., USA). The capsules showed a mean particle size of 200-400 nm which is appropriate for dermal application Comparative Examples 3-4. Composition Comprising *Pinus pinaster* Bark Extract or Curcumin The composition comprising *Pinus pinaster* bark extract (comparative example 3) was prepared by dissolving said extract in distilled water and vortexing.

The composition comprising Curcumin (comparative example 4) was prepared by dissolving a said compound in an aqueous solution of dimethysulphoxide (0.1 wt %) and vortexing.

The compositions are provided in Table 2 below, wherein the amounts are expressed as wt % with respect to the total weight of the composition.

TABLE 2

|  | Comparative Example 3 | Comparative Example 4 |
|---|---|---|
| *Pinus pinaster* bark extract | 1 | — |
| Curcumin | — | 0.01 |
| Water q.s. | 100 | 100 |

Comparative Examples 5-7. Unloaded Capsules and Capsules Loaded with *Pinus pinaster* Bark Extract or Curcumin Unloaded capsules (comparative example 5) were prepared by the high shear homogenization method. Phospholipid from Phosphotech (having the same composition has described in example 2) was dispersed in water and mixed vigorously. Capsules suspension was homogenized using ULTRA-TURRAX (IKA® T25) at 24,000 rpm.

Capsules loaded with *Pinus pinaster* Bark Extract (comparative example 6) were prepared by the high shear homogenization method. Previously, *Pinus pinaster* bark extract (obtained from Henkel Corporation) was dissolved in water and, subsequently, the phospholipid from Phosphotec (having the same composition has described in example 2), was added and mixed vigorously. Capsule suspension was homogenized using ULTRA-TURRAX (IKA® T25).

Capsules loaded with Curcumin (comparative example 7) were prepared by the high shear homogenization method. Curcumin (obtained from Sigma-Aldrich) was dissolved in Caprylic/capric triglyceride. Then, water was added and mixed vigorously. Subsequently, the phospholipid (from Phosphotec having the same composition has described in example 2) was added and mixed vigorously. Capsule suspension was homogenized using ULTRA-TURRAX (IKA® T25).

The amount of each ingredient in the resulting compositions (capsules dispersed in water) is provided in Table 3 below, wherein the amounts are expressed as wt % with respect to the total weight of the composition.

TABLE 3

|  | Comparative Example 5 | Comparative Example 6 | Comparative Example 7 |
|---|---|---|---|
| *Pinus pinaster* bark extract | — | 1 | — |
| Curcumin | — | — | 0.01 |
| Phosphotech phospholipids* | 4 | 4 | 4 |
| Caprylic/capric triglyceride | — | 1 | 1 |
| Water q.s. | 100 | 100 | 100 |

Example 8. Inhibitory Effect on $PGE_2$ Release in Cell Culture: Inflammation Induction by Interleukin 1 Alpha (IL1a)

The inhibitory effect on IL1a inflammatory induction of the non-encapsulated composition of *Pinus pinaster* bark extract and curcumin, capsules loaded with *Pinus pinaster* bark extract and curcumin, unloaded capsules, non-encapsulated composition of *Pinus pinaster* bark extract and non-encapsulated composition of curcumin were analysed on human dermal fibroblasts.

Human dermal fibroblasts (LIFE TECHNOLOGIES), seeded in a 96-well plate up to 80% confluency, were treated with the following compositions dissolved in medium DMEM (Dulbecco's Modified Eagle Medium) to a total volume of 1 ml:

a) pine bark extract (1%)
b) curcumin (0.01%)
c) Phosphotech phospholipids (having the same composition has described in example 2) (4%)
d) curcumin (0.01%)+pine bark extract (1%)
e) capsules (curcumin (0.01%)+pine bark extract (1%)+ Phosphotech phospholipids (having the same composition has described in example 2) (4%))

for 48 hours. The inflammatory response was inducing by interleukin IL1a (5 pM in DMEM). A control was performed without applying any treatment composition and without any IL1a-induced inflammation (control) as well as without applying any treatment composition but inducing inflammation (IL1a-induced fibroblasts). After 24 hours inhibitory effect on $PGE_2$ in culture cell was measured using prostaglandin E2 EIA kit (Prostaglandin E2 EIA kit—Monoclonal (Item: 514010) Cayman Chemical).

The results are provided in Table 4 below wherein the $PGE_2$ release is expressed in pg/ml. The reduction vs IL1a-induced fibroblasts is calculated as the result of $PGE_2$ obtained for each treatment/the result of $PGE_2$ obtained for IL1a-induced fibroblasts (without any treatment). The estimated $PGE_2$ for Example 1 is calculated as the product of the result of $PGE_2$ obtained for IL1a-induced fibroblasts (2170 pg/ml) and the previously calculated reduction(s) vs IL1a-induced fibroblasts of each component when used alone according to composition a (0.400) and composition b (0.232). The estimated $PGE_2$ for composition e is calculated as the product of the result of PGE$_2$ obtained for IL1a-induced fibroblasts (2170 pg/ml) and the previously calculated reduction(s) vs IL1a-induced fibroblasts of the non-encapsulated combination of *Pinus pinaster* bark extract and curcumin according to composition d (0.071) and the unloaded capsules according to composition c (0.622).

TABLE 4

| | PGE$_2$ (pg/ml) | Calculated reduction vs IL1a-induced fibroblasts | Estimated PGE$_2$ (pg/ml) |
|---|---|---|---|
| Control | 471 | — | — |
| Ila-induced fibroblasts | 2170 | — | — |
| Composition a | 868 | 0.400 | — |
| Composition b | 503 | 0.232 | — |
| Composition c | 1350 | 0.622 | — |
| Composition d | 153 | 0.071 | 201.4 |
| Composition e | 9 | 0.004 | 95.83 |

As it can be seen in Table 4 when comparing the data of observed PGE$_2$ and estimated PGE$_2$, a synergistic effect was observed between *Pinus pinaster* bark extract and curcumin were administered in combination both as a non-encapsulated composition (composition d) and as in the form of capsules (composition e).

Further, the results of Table 4 indicate that capsules loaded *Pinus pinaster* bark extract and curcumin (composition e) have a powerful anti-inflammatory activity since they completely inhibited the release of PGE$_2$ (*p<0.05).

Example 9. Film-Forming Effect on Skin and Occlusive Potential

Atopic skin is characterized by deficiency of hydration factors and alteration in epidermal lipid metabolism (Barrier function). Occlusion effect is desired in topical formulations because it increases skin hydration.

An occlusive test was performed to compare the in vitro occlusive capacity of the following compositions: unloaded capsules (Comparative Example 5), capsules loaded with *Pinus pinaster* bark extract (Comparative Example 6), capsules loaded with curcumin (Comparative Example 7) and capsules loaded with *Pinus pinaster* bark extract and curcumin (Example 2). The test was conducted using 10 ml vials, filled with 5 ml distilled water and sealed with cellulose acetate filter with a pore size of 0.45 micrometer. A sample of each of the test compositions (300 μl) was spread over the filter and stored at 25° C. for 6, 24 and 48 h. The control was performed without applying any composition.

The occlusion factor F was calculated using the following equation:

$$F = 100 \times \frac{A - B}{A}$$

wherein A is the amount of water evaporated through the cellulose acetate membrane without applying any composition (control) and B is the amount of water evaporated through the cellulose acetate membrane after applying the test compositions. The evaporated amount of water was determined by weight loss (analytical balance Kern, Mod. ABJ 120-4M).

The results are provided in Table 5 below.

TABLE 5

| Formulation | Time (hours) | Occlusion factor F |
|---|---|---|
| Comparative Example 5 | 6 | 10 |
| | 24 | 12 |
| | 48 | 15 |
| Comparative Example 6 | 6 | 11 |
| | 24 | 12 |
| | 48 | 15 |
| Comparative Example 7 | 6 | 17 |
| | 24 | 18 |
| | 48 | 20 |
| Example 2 | 6 | 39 |
| | 24 | 40 |
| | 48 | 42 |

The results of the in vitro occlusive effect showed that no significant differences (*p<0.05) in the occlusion factor F were found between 6 and 48 hours. This results indicate that the loaded and unloaded capsules maintain the film-forming effect over time. However, the capsules loaded with *Pinus pinaster* bark extract and curcumin presented a considerable unexpected increase (synergistic effect) in the occlusion factor F.

Example 10. In Vivo Anti-Redness Efficacy

Subjects suffering from atopic dermatitis, often display erythema lesions (red areas) spots that may occur in various areas of the body, such as the face. To assess the efficacy of the composition of example 2 when incorporated into a cream formulation in a blind test, ten female subjects prone to atopic skin, exhibiting redness on the face, were selected. Subjects were asked to apply cream A and cream B (example 2), hemiface twice a day for 27 days. The number and area of red spots present were measured at day 0 and day 28, by taking standardized photographic images obtained with normal, cross-polarized and UV light, of both hemifaces and the front, using VISTA® Complexation Analysis system (Canfield Scientific, Inc., USA). The integrated analysis software allows the definition of a Region of Interest and the calculation of the areas and number of the red spots. For the imaging system a mask for the defined area is created, and applied in the subsequent images to calculate the differences against day 0.

The results are provided in Table 6, expressed in percentage of the difference in the number of red-spot and in the area covered by said red spots between D0 and D28. As it can be seen, cream B (comprising the composition of example 2) reduced the number or red spots by 3.6%, and the red spot area by 4.7%, whereas cream A shows an increase in red spots number and area, of 9.4% and 8.5% respectively. Thus, the application of cream B resulted in an overall decrease of 13% in the number of red spots, and 13.2% of the red snot area.

TABLE 6

| | Formulation | | | | | |
|---|---|---|---|---|---|---|
| | Cream A | | | Cream B | | |
| | Day 0 | Day 28 | % of change | Day 0 | Day 28 | % of change |
| Count of red spots (mean, n = 10) | 173.3 | 189.5 | +9.4 | 188.1 | 181.4 | −3.6 |

TABLE 6-continued

| | Formulation | | | | | |
|---|---|---|---|---|---|---|
| | Cream A | | | Cream B | | |
| | Day 0 | Day 28 | % of change | Day 0 | Day 28 | % of change |
| Area of red spots (mean, n = 10) | 9.4 | 10.2 | +8.5 | 10.6 | 10.1 | −4.7 |

Example 11. In Vivo Barrier Function Recovery

Atopic skin is characterized by having a lower level of lipids (which ensure a normal barrier function of skin) than normal skin. This leads, among other disturbances, to an increased trans-epidermal water loss (TEWL). This defect in the barrier function of the skin, leads to dryer skin, exacerbating the itchiness discomfort associated with dermatitis, further worsening atopic skin manifestations.

The efficacy of cream B (comprising the composition of example 2) in improving (or restoring) the barrier function of the skin, was performed by performing the plastic occlusion stress test (POST). POST is a well-known, dynamic approach for studying the skin barrier function, by evoking an over-stimulation of the cutaneous water assessed by TEWL measurement. TEWL (g/m$^2$ h) is expressed as the relation between the amount of water g transported, by area, in m$^2$, over a determined period of time, in h.

Subjects applied the compositions cream A or cream B on the forearm, two times a day for one week. Insult to the skin, was induced on day seven, by applying an occlusion patch for 24 h. The occlusion patch had a surface of 5 cm×5 cm and comprised a layer of gauze, followed by subsequent layers of Parafilm™ (Neenah, Wis., United States), cling film and Parafilm™. The occlusion patch is applied to the center part of the forearm, and secured with Durapore® adhesive (3M, Nadarzyn, Poland). On day eight, after removal of the occlusion patch, TEWL was measured every minute for thirty minutes, in order to evaluate the time needed for the skin to reduce the water loss to half after the insult. Thus indicating the speed of recovery of the barrier function and regeneration of the stratum corneum. Measurements were performed using a Tewameter® TM300 (Courage+Khazaka Electronics GmbH, Köln, Germany). The results are shown in Table 7, and are expressed as the time required in minutes, for the skin to reduce its' water loss to half (50%). As it can be seen, skin treated with cream B showed a decrease in the time required to reduce the water loss, when compared to skin treated with cream B, 4 minutes vs ca 10 minutes, which translates into a 60% improvement.

TABLE 7

| Formulation | Mean t$_{1/2}$ (min) |
|---|---|
| Cream A | 9.88 |
| Cream B | 4.00 |
| Difference (%) | −60% |

The compositions of the creams used in examples 10 and 11 are as follows:

TABLE 8

| Ingredients | Cream A (% in weight) | Cream B (% in weight) |
|---|---|---|
| Deioniozed water | up to 100% | up to 100% |
| Paraffinum liquidum | 5-10% | 5-10% |
| Glycerin | 2-5% | 2-5% |
| Isopropyl myristate | 2-5% | 2-5% |
| Caprylic/Capric Triglyceride | 2-5% | 2-5% |
| Steareth-7 | 2-5% | 2-5% |
| Stearyl alcohol | 1-5% | 1-5% |
| Cetearyl octanoate | 0.2-1% | 0.2-1% |
| Ceteareth-15 | 0.2-1% | 0.2-1% |
| Glyceryl stearate | 0.2-1% | 0.2-1% |
| Composition of Example 2 | — | 2% |

Cream B, was prepared by adding 2% weight from the composition of example 2 to the corresponding amount of cream A. To ensure the correct homogeneity of the cream, after addition of the composition of example 2, the cream was stirred for 30 minutes.

The invention claimed is:

1. A composition comprising *Pinus pinaster* bark extract and curcumin wherein the ratio by weight of curcumin to *Pinus pinaster* bark extract is from 1:70 to 1:125.

2. The composition according to claim 1, further comprising water.

3. A microcapsule and/or nanocapsule comprising a composition as defined in claim 1.

4. The microcapsule and/or nanocapsule according to claim 3, which comprises a phospholipid bilayer.

5. The microcapsule and/or nanocapsule according to claim 4, wherein the phospholipid is selected from the group consisting of phosphatidylcholine, phosphatidylethanolamine, phosphatidylinositol, phosphatidylserine, phosphatidic acid, and mixtures thereof.

6. The microcapsule and/or nanocapsule according to claim 4, wherein the phospholipid comprises omega-3 fatty acids.

7. The microcapsule and/or nanocapsule according to claim 3, further comprising a medium chain triglyceride comprising two or three fatty acids having from 6 to 12 carbon atoms.

8. The microcapsule and/or nanocapsule according to claim 7, wherein the ratio by weight of curcumin to medium chain triglyceride is from 1:10 to 1:1000.

9. The microcapsule and/or nanocapsule according to claim 3, further comprising vitamin E or an ester thereof and astaxanthin.

10. A composition comprising microcapsules and/or nanocapsules as defined in claim 3.

11. The composition according to claim 10, wherein the microcapsules and/or nanocapsules are dispersed in a matrix comprising a pharmaceutically acceptable excipient selected from the group consisting of water, humectants, preservatives, and mixtures thereof.

12. The composition according to claim 10, which is suitable for topical use.

13. A method of treating patients with atopic dermatitis by topically applying to said patient a composition according to claim 1.

14. A method of treating patients with atopic dermatitis by topically applying to said patient a microcapsule and/or nanocapsule according to claim 3.

15. A method of reducing redness and skin water-loss in a patient prone to atopic dermatitis by topically applying a composition according to claim 1.

16. A method of reducing redness and skin water-loss in a patient prone to atopic dermatitis by topically applying a microcapsule and/or nanocapsule according to claim 3.

* * * * *